(12) United States Patent
Higuchi

(10) Patent No.: US 12,053,158 B2
(45) Date of Patent: Aug. 6, 2024

(54) TREATMENT SYSTEM

(71) Applicant: OLYMPUS CORPORATION, Tokyo (JP)

(72) Inventor: Tatsuya Higuchi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 867 days.

(21) Appl. No.: 17/077,443

(22) Filed: Oct. 22, 2020

(65) Prior Publication Data
US 2021/0038059 A1    Feb. 11, 2021

Related U.S. Application Data

(63) Continuation of application No. PCT/JP2018/016978, filed on Apr. 26, 2018.

(51) Int. Cl.
*A61B 1/00* (2006.01)
*A61B 17/295* (2006.01)
*A61B 17/32* (2006.01)
*A61B 17/00* (2006.01)

(52) U.S. Cl.
CPC ...... *A61B 1/00154* (2013.01); *A61B 1/00082* (2013.01); *A61B 1/00135* (2013.01); *A61B 17/295* (2013.01); *A61B 17/320016* (2013.01); *A61B 2017/0034* (2013.01); *A61B 2017/00818* (2013.01)

(58) Field of Classification Search
CPC .......... A61B 17/295; A61B 17/320016; A61B 2017/0034; A61B 1/00154; A61B 1/00082; A61B 1/00135; A61B 1/018
See application file for complete search history.

(56) References Cited

U.S. PATENT DOCUMENTS

| 4,465,481 A | * | 8/1984 | Blake | A61M 27/00 604/541 |
|---|---|---|---|---|
| 5,236,231 A | * | 8/1993 | Allen | F16L 15/003 285/55 |
| 2003/0233025 A1 | | 12/2003 | Saadat et al. | |

(Continued)

FOREIGN PATENT DOCUMENTS

| CN | 107205619 A | 9/2017 |
|---|---|---|
| EP | 2762054 A1 | 8/2014 |

(Continued)

OTHER PUBLICATIONS

International Search Report dated Jul. 24, 2018 issued in PCT/JP2018/016978.

(Continued)

*Primary Examiner* — Tuan V Nguyen
(74) *Attorney, Agent, or Firm* — Scully, Scott, Murphy & Presser, P.C.

(57) ABSTRACT

A treatment system includes a guide sheath provided with a pre-curved portion that has been preliminarily curved in a direction intersecting a longitudinal axis at a distal end of a tubular sheath body having the longitudinal axis, and an overtube forming a first lumen through which the guide sheath is passed and a second lumen through which an endoscope is passed, in which a cross-sectional shape of an inner peripheral surface defining the first lumen has a shape configured to house the guide sheath in a state where the pre-curved portion remains curved.

19 Claims, 12 Drawing Sheets

(56) References Cited

U.S. PATENT DOCUMENTS

| | | |
|---|---|---|
| 2003/0233026 A1 | 12/2003 | Saadat et al. |
| 2003/0233027 A1 | 12/2003 | Ewers et al. |
| 2003/0233056 A1 | 12/2003 | Saadat et al. |
| 2008/0183184 A1 | 7/2008 | Kaye et al. |
| 2008/0188868 A1 | 8/2008 | Weitzner et al. |
| 2008/0188869 A1 | 8/2008 | Weitzner et al. |
| 2008/0188871 A1 | 8/2008 | Smith et al. |
| 2008/0188890 A1 | 8/2008 | Weitzner et al. |
| 2008/0221391 A1 | 9/2008 | Weitzner et al. |
| 2008/0243176 A1 | 10/2008 | Weitzner et al. |
| 2011/0224494 A1 | 9/2011 | Piskun et al. |
| 2012/0004502 A1 | 1/2012 | Weitzner et al. |
| 2013/0144118 A1 | 6/2013 | Piskun et al. |
| 2013/0231534 A1 | 9/2013 | Piskun et al. |
| 2013/0274553 A1 | 10/2013 | Piskun et al. |
| 2013/0331645 A1 | 12/2013 | Yamatani et al. |
| 2013/0345511 A1 | 12/2013 | Piskun et al. |
| 2013/0345519 A1 | 12/2013 | Piskun et al. |
| 2014/0142393 A1 | 5/2014 | Piskun et al. |
| 2015/0025314 A1 | 1/2015 | Piskun et al. |
| 2015/0157192 A1 | 6/2015 | Piskun et al. |
| 2015/0209024 A1 | 7/2015 | Piskun et al. |
| 2015/0223798 A1 | 8/2015 | Piskun et al. |
| 2015/0238180 A1 | 8/2015 | Weitzner et al. |
| 2015/0265818 A1 | 9/2015 | Piskun et al. |
| 2015/0272564 A1 | 10/2015 | Piskun et al. |
| 2015/0282800 A1 | 10/2015 | Piskun et al. |
| 2015/0297209 A1 | 10/2015 | Piskun et al. |
| 2015/0313584 A1 | 11/2015 | Piskun et al. |
| 2015/0335324 A1 | 11/2015 | Piskun et al. |
| 2016/0015252 A1 | 1/2016 | Piskun et al. |
| 2016/0051128 A1 | 2/2016 | Piskun et al. |
| 2016/0089007 A1 | 3/2016 | Weitzner et al. |
| 2016/0228113 A1 | 8/2016 | Weitzner et al. |
| 2016/0278757 A1 | 9/2016 | Piskun et al. |
| 2016/0309996 A1 | 10/2016 | Piskun et al. |
| 2016/0310124 A1 | 10/2016 | Piskun et al. |
| 2016/0338572 A1 | 11/2016 | Piskun et al. |
| 2016/0374658 A1 | 12/2016 | Piskun et al. |
| 2017/0079636 A1 | 3/2017 | Piskun et al. |
| 2017/0135567 A1 | 5/2017 | Piskun et al. |
| 2017/0196549 A1 | 7/2017 | Piskun et al. |
| 2017/0251907 A1 | 9/2017 | Piskun et al. |
| 2017/0007345 A1 | 11/2017 | Smith et al. |
| 2017/0311790 A1 | 11/2017 | Yoshida |
| 2017/0325662 A1 | 11/2017 | Piskun et al. |
| 2019/0231466 A1 | 8/2019 | Weitzner et al. |
| 2020/0163733 A1 | 5/2020 | Smith et al. |

FOREIGN PATENT DOCUMENTS

| | | |
|---|---|---|
| EP | 3 248 532 A1 | 11/2017 |
| JP | H06-181879 A | 7/1994 |
| JP | 2006-505302 A | 2/2006 |
| JP | 2010-511440 A | 4/2010 |
| JP | 2010-516435 A | 5/2010 |
| JP | 2013-514827 A | 5/2013 |
| JP | 2016-526397 A | 9/2016 |
| WO | WO 2003/105563 A2 | 12/2003 |
| WO | WO 2008/070556 A1 | 6/2008 |
| WO | WO 2008/094931 A2 | 8/2008 |
| WO | WO 2011/084616 A2 | 7/2011 |
| WO | WO 2013/047723 A1 | 4/2013 |
| WO | WO 2014/200737 A1 | 12/2014 |
| WO | WO 2018/047340 A1 | 3/2018 |

OTHER PUBLICATIONS

Chinese Office Action dated Mar. 29, 2024 received in 201880092199.1.

\* cited by examiner

TREATMENT SYSTEM

CROSS-REFERENCE TO RELATED APPLICATIONS

This is a continuation of International Application PCT/JP2018/016978 which is hereby incorporated by reference herein in its entirety.

TECHNICAL FIELD

The present invention relates to a treatment system.

BACKGROUND ART

There is a known system including a catheter having a lumen penetrating in a longitudinal direction, a guide sheath inserted into the lumen and protruding from a distal end of the catheter, and a treatment tool that is guided to the distal end of the catheter by means of the guide sheath and that treats an affected area (for example, refer to PTL 1).

The guide sheath is formed of a relatively hard material, and a distal end portion of the guide sheath tends to keep its curved shape. The guide sheath is deformed to be in a substantially straight line when placed in the lumen, and when exposed from the lumen, the guide sheath tries to return to its curved shape.

CITATION LIST

Patent Literature

{PTL 1} Japanese Translation of PCT International Application, Publication No. 2016-526397

SUMMARY OF INVENTION

According to an aspect of the present invention, a treatment system includes a guide sheath having a pre-curved portion that has been preliminarily curved in a direction intersecting a longitudinal axis at a distal end of a tubular sheath body having the longitudinal axis; and an overtube having a first lumen through which the guide sheath is passed and a second lumen through which an endoscope is passed, wherein an inner peripheral surface defining the first lumen has a cross-sectional shape configured to house the guide sheath in a state where the pre-curved portion remains curved.

According to another aspect of the present invention, an overtube includes an elongated tube body having a first lumen and a second lumen each of which is passed through the tube body in a direction of a longitudinal axis, wherein an inner peripheral surface forming the first lumen has a constant cross-sectional shape in a direction orthogonal to the longitudinal axis over an entire length of the tube body, and the cross-sectional shape includes a circular portion having an inner diameter dimension larger than an outer diameter dimension of the second lumen, and a groove portion that is recessed radially outward in at least a part of the circular portion in a circumferential direction.

According to further another aspect of the present invention is a method for peeling tissue inside a body cavity using a guide sheath having a pre-curved portion that has been preliminarily curved in a direction intersecting a longitudinal direction of a hollow tube body at a distal end of the tube body, an overtube having a first lumen through which the guide sheath is passed and a second lumen through which an endoscope is passed, and the endoscope, the method including: inserting the endoscope into the body cavity; inserting the overtube into the body cavity using the endoscope inserted in the second lumen as a guide; inserting the guide sheath into the first lumen; rotating the guide sheath on a central axis of the longitudinal direction of the tube body so that the pre-curved portion is curved downward on an image of the endoscope; inserting forceps for grasping the tissue into the guide sheath and protruding a distal end of the forceps from the pre-curved portion; pulling the tissue by the forceps; inserting an incision instrument into a channel of the endoscope from a proximal end side and protruding the incision instrument from a distal end of the channel; incising, using the incision instrument, the tissue pulled by the forceps; and discharging the incised tissue outside the body cavity while being grasped by the forceps.

DESCRIPTION OF EMBODIMENTS

A treatment system 1 according to an embodiment of the present invention will be described below with reference to the drawings.

Figure 1:
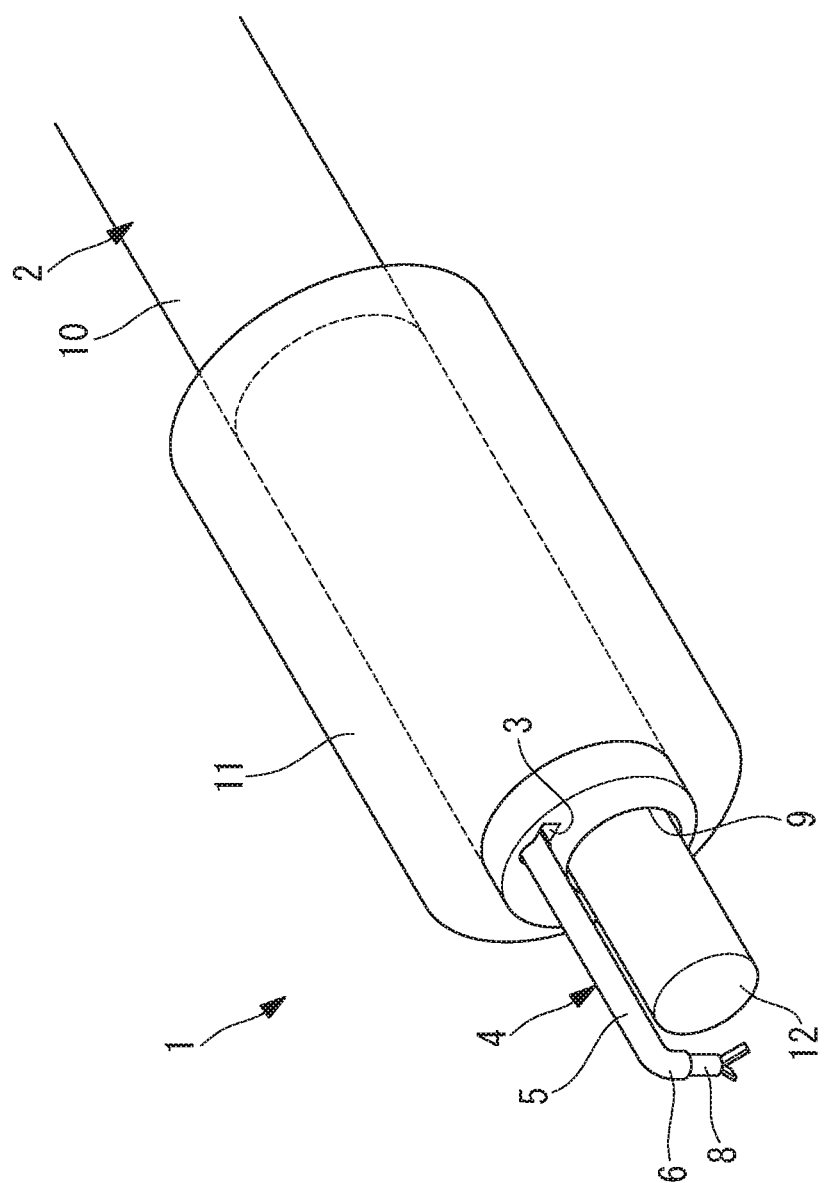
FIG. 1 is a partial perspective view illustrating a treatment system according to an embodiment of the present invention.

As illustrated in FIG. 1, the treatment system 1 according to the present embodiment includes an overtube 2 that is to be inserted into a body cavity of a patient, and a guide sheath 4 that is to be inserted into one lumen (first lumen) 3 of the overtube 2.

Figure 2:
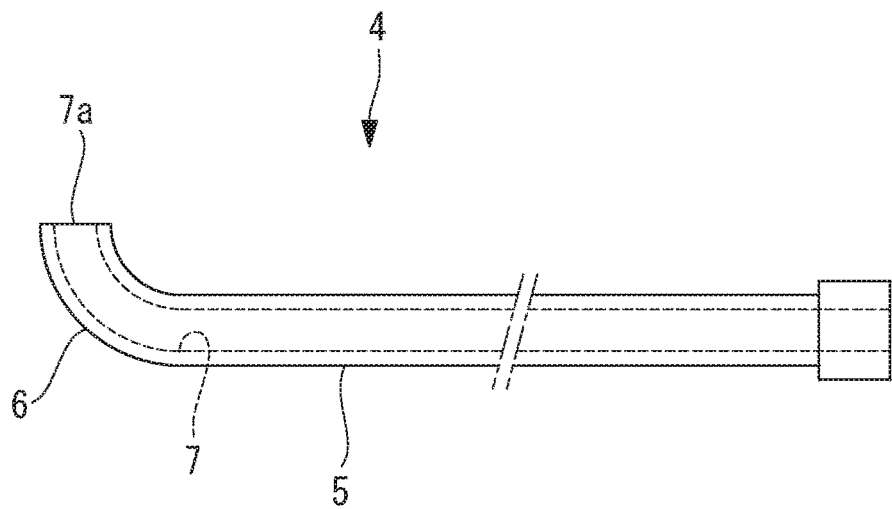
FIG. 2 is a side view illustrating a guide sheath forming the treatment system in FIG. 1.

As illustrated in FIG. 2, the guide sheath 4 includes a cylindrical tubular sheath body 5 having a longitudinal axis, and a pre-curved portion 6 in which a distal end of the sheath body 5 is pre-curved in a direction intersecting the longitudinal axis. The guide sheath 4 has an inner hole 7 extending over the entire length. A treatment tool 8 such as grasping forceps is inserted into the inner hole 7 from a proximal end side.

The treatment tool 8 is guided to a distal end side of the guide sheath 4 through the inner hole 7 and made to protrude from an opening 7a disposed at a distal end of the pre-curved portion 6. The guide sheath 4 is formed of a relatively hard elastic material, and even if the treatment tool 8 is inserted into the inner hole 7, the pre-curved portion 6 maintains a curved shape.

The overtube 2 includes a multi-lumen tube 10 including two lumens (first lumen, second lumen) 3 and 9 integrally formed of a solid long resin material and penetrating over the entire length thereof, and a balloon 11 that is disposed on an outer peripheral surface of a distal end portion of the multi-lumen tube 10 and that expands radially outward through the supply of a fluid.

The multi-lumen tube 10 is formed of an elastic material having a Shore hardness of 35A or more and 45A or less. The guide sheath 4 is formed of a material having a Shore hardness of 65D or more and 75D or less.

The multi-lumen tube 10 includes the first lumen 3 into which the guide sheath 4 is inserted and the second lumen 9 into which an endoscope 12 is inserted.

The second lumen 9 has a constant cross-sectional shape over the entire length thereof. The cross-sectional shape of the second lumen 9 is a circle having an inner diameter slightly larger than the outer diameter of the endoscope 12.

Figure 3:
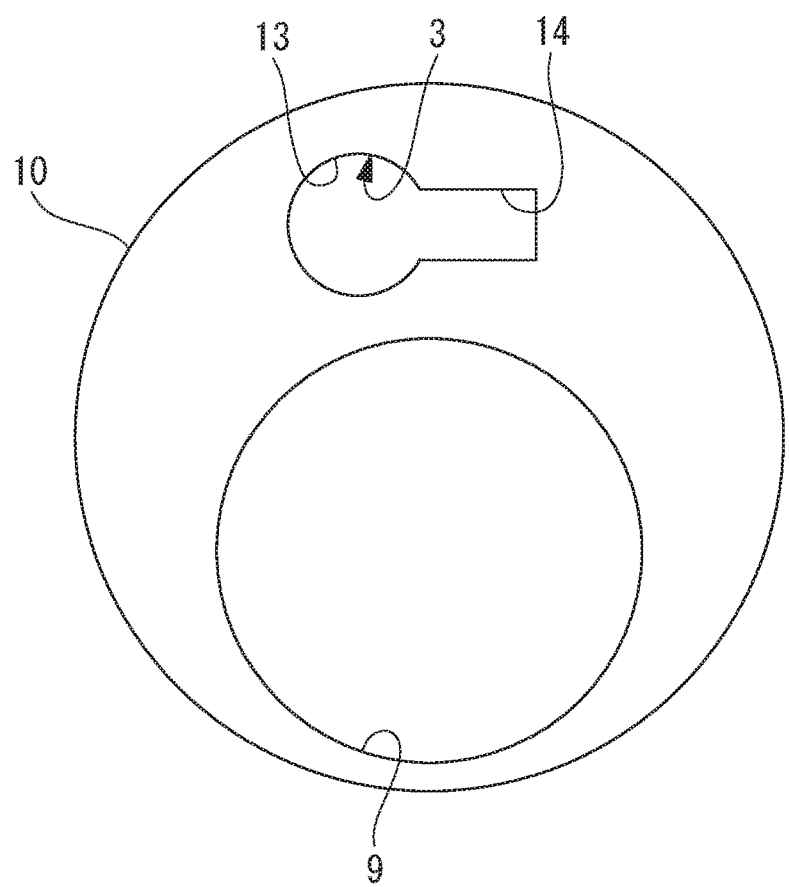
FIG. 3 is a front view illustrating a distal end surface of an overtube forming the treatment system in FIG. 1.
Figure 4:
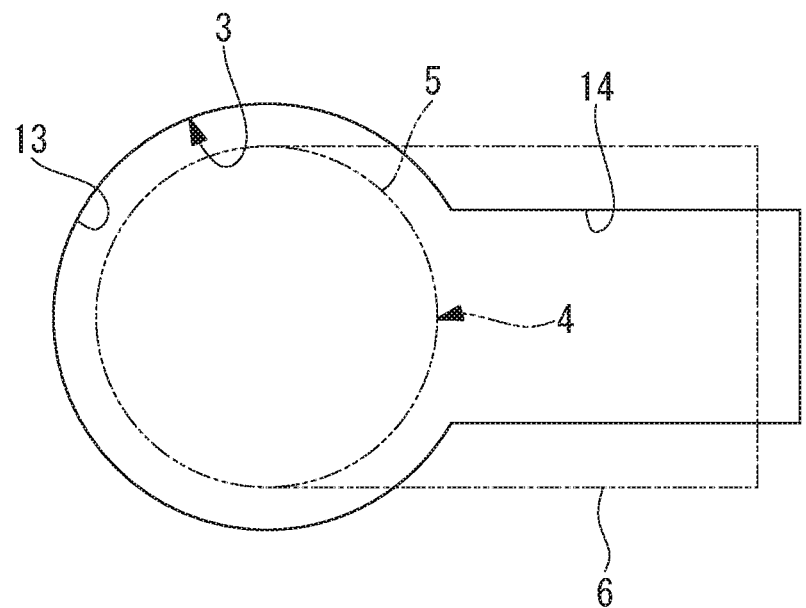
FIG. 4 is an enlarged view illustrating the relationship between a first lumen of the overtube in FIG. 3 and the guide sheath.

The first lumen 3 also has a constant cross-sectional shape over the entire length thereof. As illustrated in FIGS. 3 and 4, the cross-sectional shape of the first lumen 3 is a shape having a circular portion 13 having an inner diameter slightly larger than an outer diameter of the guide sheath 4 and a groove portion 14 in which a part of the circular portion 13 in a circumferential direction is recessed radially outward. That is, the inner peripheral surface that defines the first lumen 3 has the groove portion 14 that is recessed radially outward in a part of the inner surface of the cylinder in the circumferential direction. In addition, regarding the cross-sectional shape of the first lumen 3, it is preferable that a dimension (second dimension) along a direction (second direction) intersecting the arrangement direction of the first lumen 3 and the second lumen 9 be larger than a dimension (first dimension) along the arrangement direction (first direction) of the first lumen 3 and the second lumen 9.

As illustrated in FIG. 4, the groove width dimension of the groove portion 14 is slightly smaller than the outer diameter dimension of the guide sheath 4. The groove width dimension of the groove portion 14 is 40% to 60% of an outer diameter dimension of the guide sheath 4. The depth dimension of the groove portion 14 is larger than the length of the pre-curved portion 6 of the guide sheath 4 protruding radially from the sheath body 5.

The operation of the treatment system 1 according to the present embodiment configured as described above will be described below.

Figure 5:
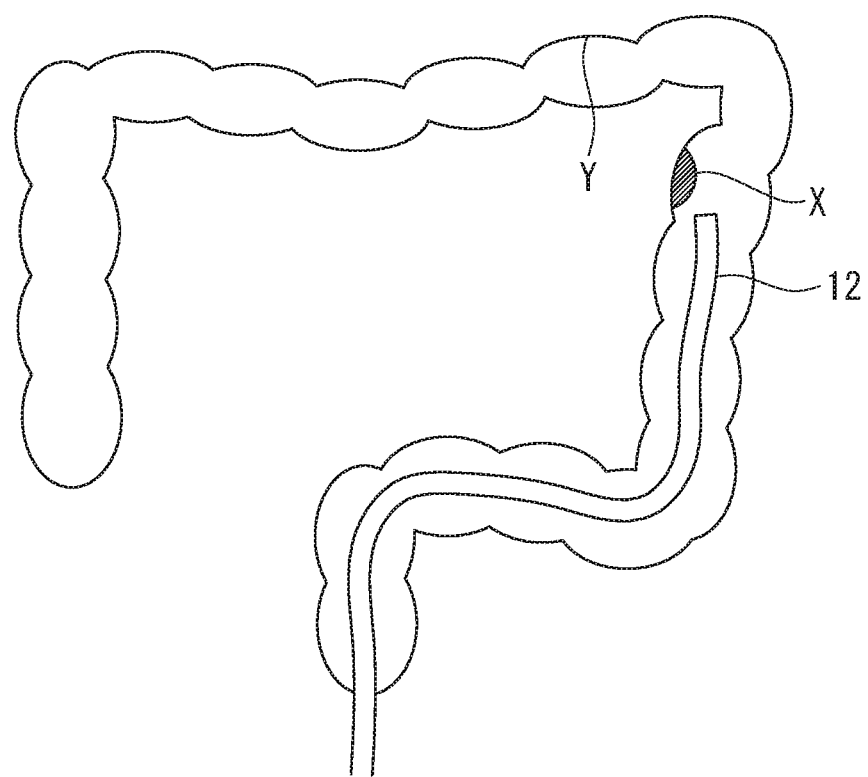
FIG. 5 is a schematic view illustrating a state in which an endoscope is inserted into a body cavity in a method of treating an affected part in a body cavity using the treatment system in FIG. 1.

In order to treat an affected part X in a body cavity Y using the treatment system 1 according to the present embodiment, first, as illustrated in FIG. 5, the treatment system 1 is inserted into the body cavity Y while observing the body cavity Y with the endoscope 12.

Figure 6:
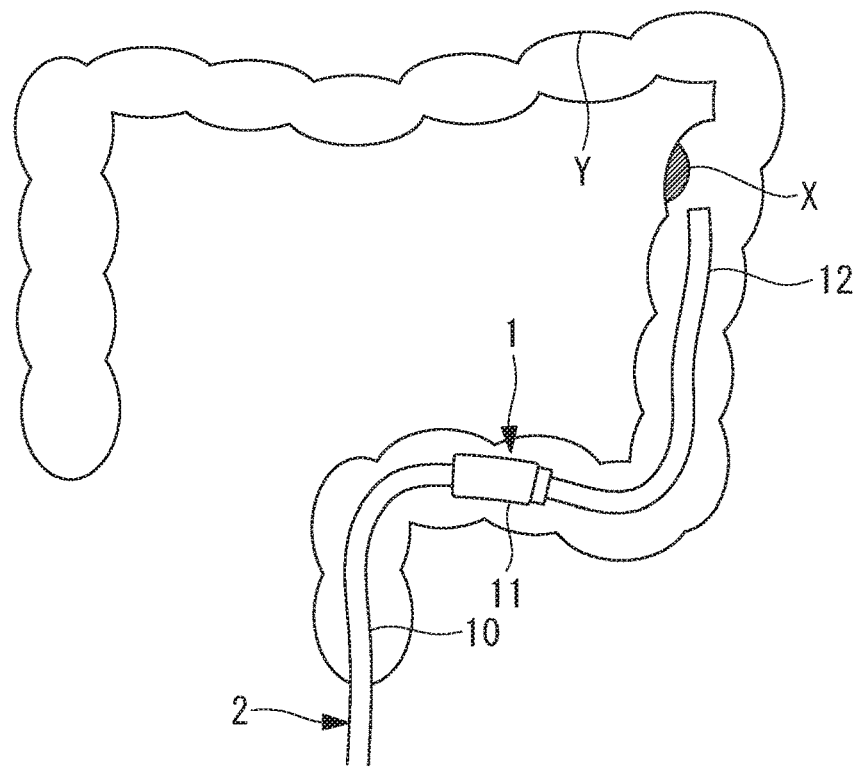
FIG. 6 is a schematic view illustrating a process of inserting the overtube into the body cavity after the state illustrated in FIG. 5.

Next, as illustrated in FIG. 6, when a distal end of the endoscope 12 has been inserted to a position where the affected part X in the body cavity Y can be observed, the overtube 2 is inserted into the body cavity Y using the endoscope 12 inserted in the second lumen 9 as a guide.

Figure 7:
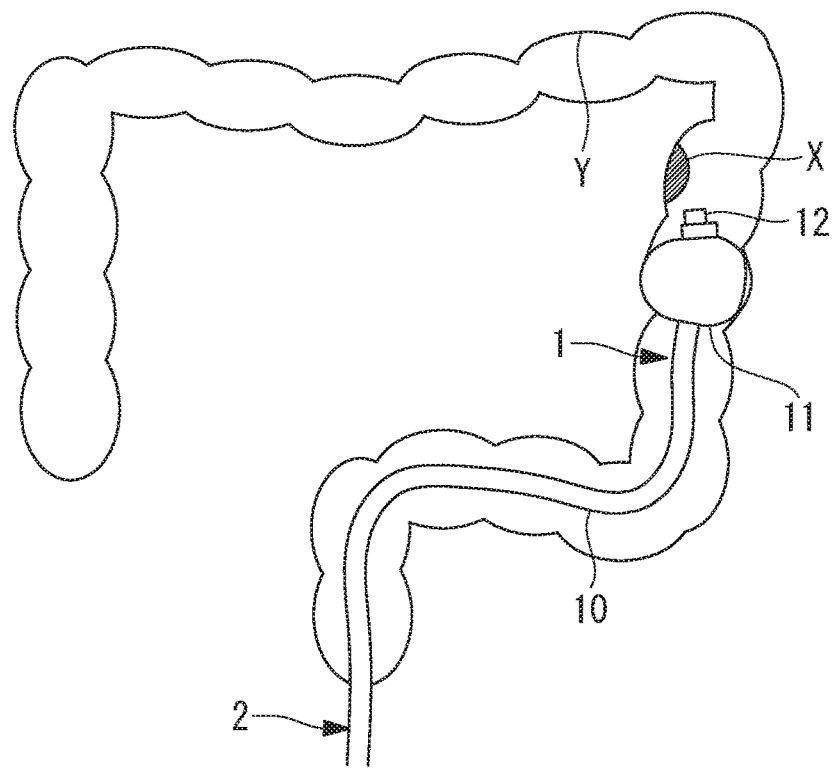
FIG. 7 is a schematic view illustrating a state in which a balloon provided in the overtube is expanded after the state illustrated in FIG. 6.

When the overtube 2 has been inserted into the endoscope 12 up to a predetermined forward/backward direction position, the overtube 2 is rotated in a circumferential direction around the endoscope 12 serving as an axis. As a result, the circular portion 13 of the first lumen 3 is disposed on the opposite side to the affected area X with the endoscope 12 interposed therebetween. At this position, as illustrated in FIG. 7, the balloon 11 provided on the overtube 2 is inflated to press an outer peripheral surface of the balloon 11 against an inner peripheral surface of the body cavity Y. As a result, the overtube 2 is fixed to the body cavity Y.

In this state, the guide sheath 4 is inserted into the first lumen 3 from the proximal end of the overtube 2. The guide sheath 4 is inserted into the first lumen 3 with the pre-curved portion 6 in the groove portion 14 and the sheath body 5 in the circular portion 13.

Since the groove width dimension of the groove portion 14 of the first lumen 3 is set smaller than the outer diameter dimension of the guide sheath 4, when the pre-curved portion 6 is inserted into the groove portion 14, the pre-curved portion 6 is inserted while widening the groove width of the groove portion 14. Since the multi-lumen tube 10 is formed of an elastic material having a Shore hardness of 35A or more and 45A or less and the guide sheath 4 is formed of a material having a Shore hardness of 65D or more and 75D or less, at the time of insertion, the groove width of the groove portion 14 can be easily expanded without deforming the guide sheath 4, and the guide sheath 4 can be easily inserted into the first lumen 3.

Figure 8:
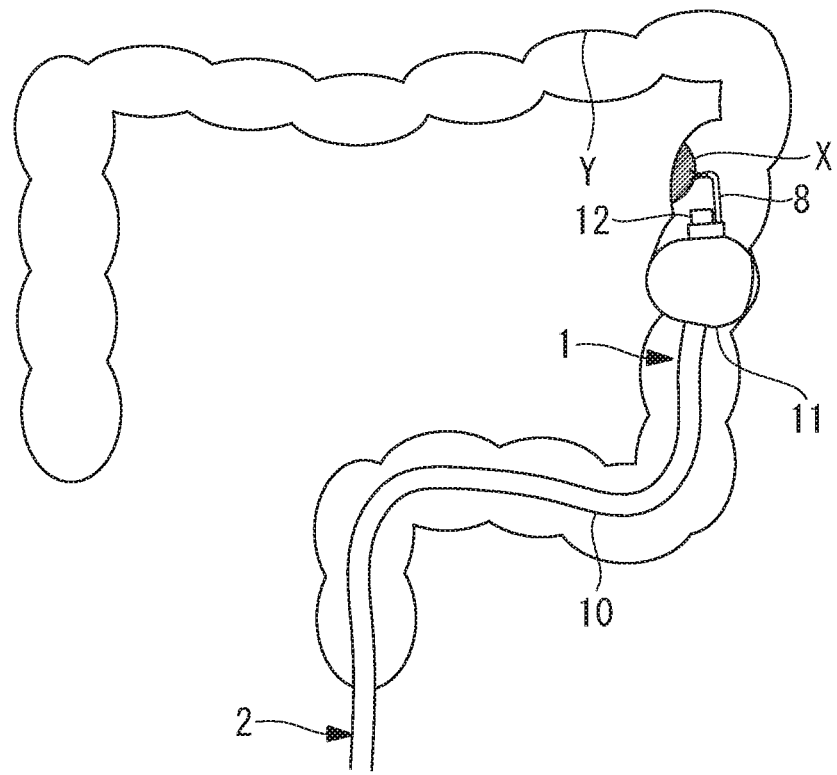
FIG. 8 is a schematic view illustrating a state in which the guide tube and the treatment tool are made to protrude from a distal end opening of the first lumen in the state in FIG. 7.

Then, when the guide sheath 4 is advanced with respect to the overtube 2 until the pre-curved portion 6 protrudes from a distal end opening of the overtube 2, as illustrated in FIG. 8, since the pre-curved portion 6 appears in the field of view of the endoscope 12, by rotating the guide sheath 4 about the longitudinal axis while observing the image of the endoscope 12, the pre-curved portion 6 is disposed in a direction in which a distal end of the pre-curved portion 6 faces the affected area.

In this state, when the treatment tool 8 is inserted into the inner hole 7 from a proximal end side of the guide sheath 4, the treatment tool 8 advances along the guide sheath 4, is curved according to the curved shape of the pre-curved portion 6, and then is made to protrude from the opening 7a at the distal end of the pre-curved portion 6. Since the distal end of the pre-curved portion 6 is disposed in a direction toward the affected area X, the treatment tool 8 protruding from the opening 7a at the distal end of the pre-curved portion 6 can easily reach the affected area X located in front.

For example, when the treatment tool 8 is grasping forceps, the affected area X can be easily grasped by the grasping forceps 8. Then, by pulling the grasping forceps 8 toward the proximal end side, the grasped tissue of the affected area X can be pulled. Then, the pulled tissue can be treated by peeling or the like by using another treatment tool such as a knife introduced through a channel of the endoscope 12.

As described above, according to the treatment system 1 of the present embodiment, because the first lumen 3 includes the circular portion 13 and the groove portion 14, it is possible to insert the guide sheath 4 into the first lumen 3 from the proximal end side in a state where the pre-curved portion 6 remains curved by disposing the sheath body 5 in the circular portion 13 and disposing the pre-curved portion 6 in the groove portion 14.

Since the multi-lumen tube 10 forming the overtube 2 is formed of a material sufficiently soft with respect to the guide sheath 4, even if the groove portion 14 is expanded by the pre-curved portion 6 and the pre-curved portion 6 is inserted therein, the pre-curved portion 6 does not have to be largely deformed. As a result, the pre-curved portion 6 can be made to protrude from a distal end of the overtube 2 without changing its curved state. Unlike the conventional method in which the pre-curved portion 6 is straightened and inserted, the curved state of the pre-curved portion 6 is maintained when the pre-curved portion 6 is made to protrude from the distal end of the overtube 2. Thereby, there is an advantage that the treatment tool 8 guided through the inner hole 7 can be accurately advanced toward the affected area X.

Since the inner diameter of the circular portion 13 of the first lumen 3 is set larger than the outer diameter of the sheath body 5, in the insertion operation of the guide sheath 4 with the sheath body 5 arranged in the circular portion 13, it is possible to suppress the generation of friction between the sheath body 5 and the inner peripheral surface of the circular portion 13 and to improve the ease of insertion.

Since the groove width dimension of the groove portion 14 of the first lumen 3 is set smaller than the outer diameter of the sheath body 5, the sheath body 5 disposed in the circular portion 13 does not slip from the circular portion 13 toward the groove portion 14 during insertion, and is stably supported while being disposed in the circular portion 13 even after the pre-curved portion 6 has been made to protrude. Accordingly, there is an advantage that the treatment tool 8 can be prevented from moving in a direction not intended by the operator when a force is applied to the distal end of the treatment tool 8 during treatment.

Figure 9:
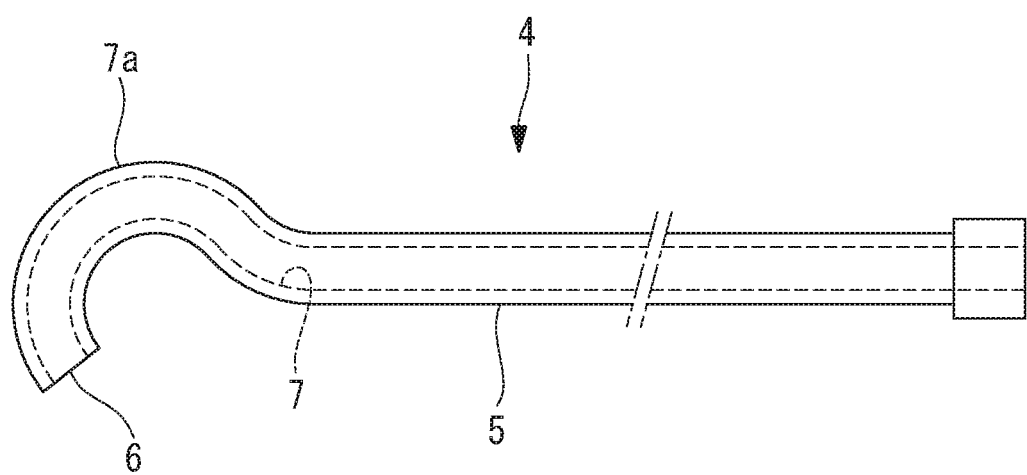
FIG. 9 is a side view illustrating a modification of the guide sheath in FIG. 2.
Figure 10:
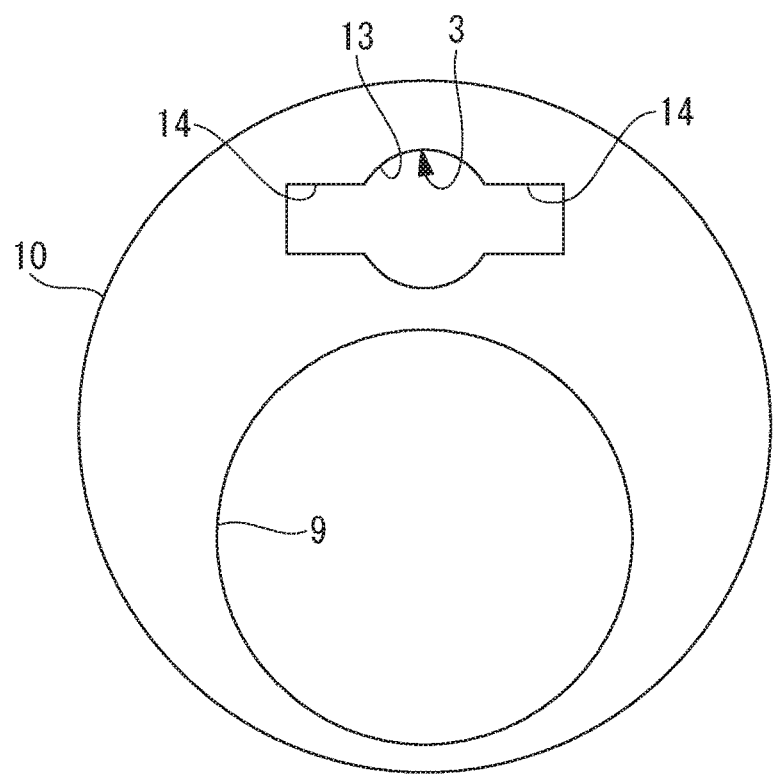
FIG. 10 is a front view illustrating a distal end surface of a modification of the overtube when the guide sheath in FIG. 9 is used.

Further, in the present embodiment, the guide sheath 4 having the pre-curved portion 6 that curves in one direction with respect to the longitudinal axis of the sheath body 5 is illustrated, but instead of this, as illustrated in FIG. 9, the guide sheath 4 having the pre-curved portion 6 protruding in two directions with respect to the longitudinal axis in the same plane with respect to the sheath body 5 may be adopted. In this case, as illustrated in FIG. 10, the shape of the first lumen 3 may have the groove portions 14 protruding on both sides with the circular portion 13 interposed therebetween.

Figure 11:
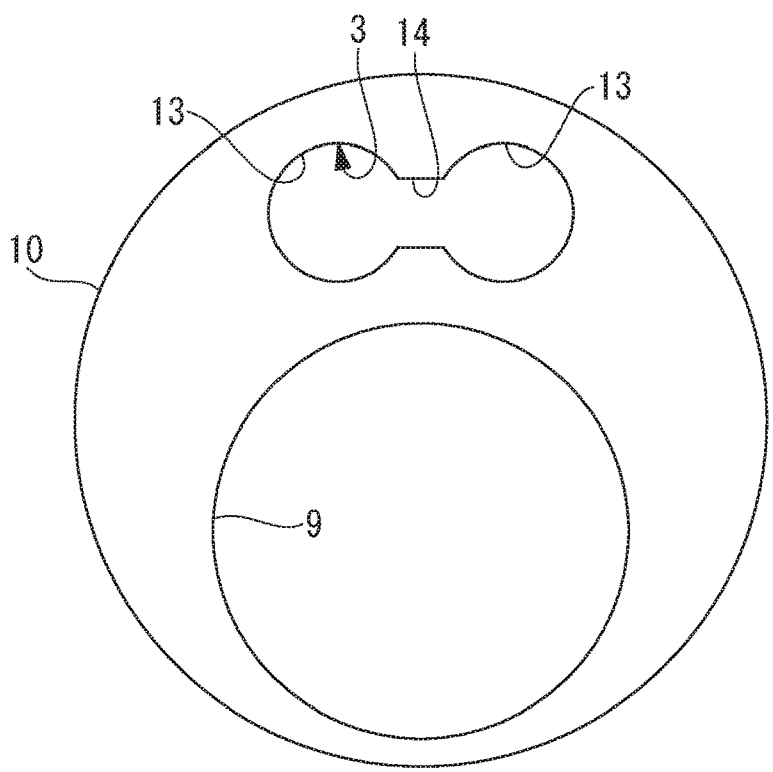
FIG. 11 is a front view illustrating a distal end surface of another modification of the overtube.

Instead of using one guide sheath 4, two may be used. In this case, the shape of the first lumen 3 may be a shape having a groove portion 14 between two circular portions 13, as illustrated in FIG. 11, and the guide sheaths 4 may be inserted one by one.

Figure 12:
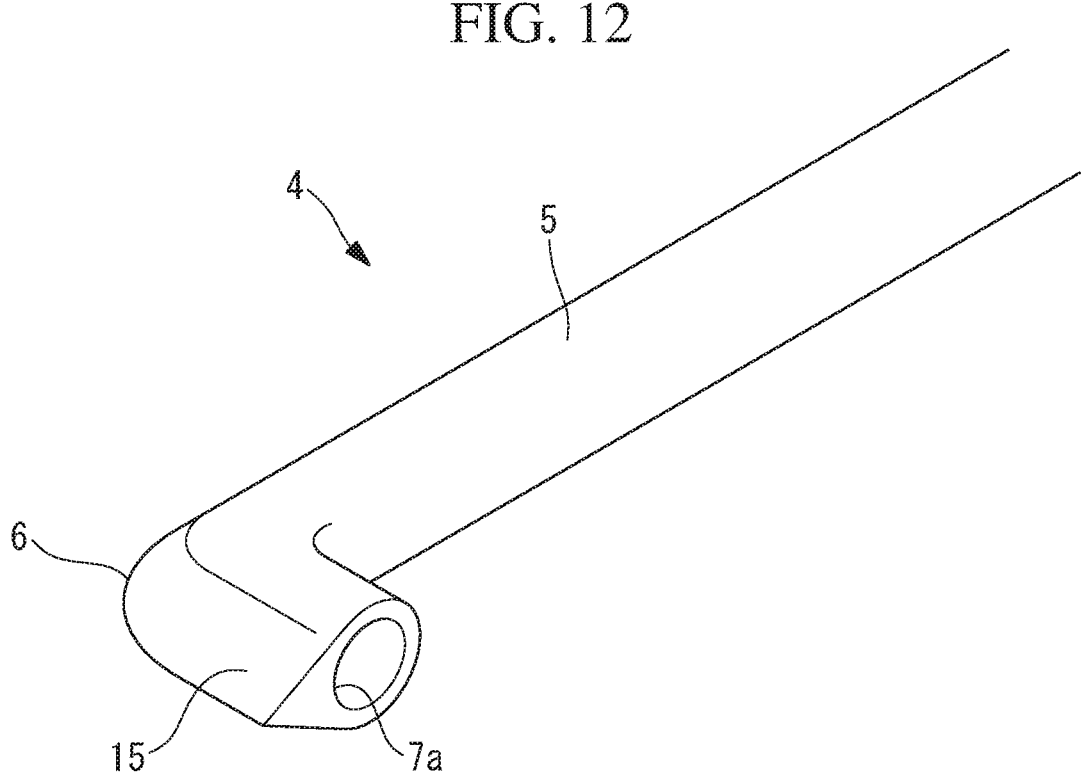
FIG. 12 is a partial perspective view illustrating the modification of the guide sheath in FIG. 2.

As the guide sheath 4, a guide sheath having a simple circular cross section is illustrated, but instead of this, as illustrated in FIG. 12, the pre-curved portion 6 may have a cross-sectional shape having an inclined surface 15 that tapers forward in the longitudinal direction of the sheath body 5. As a result, when the guide sheath 4 is advanced, while the groove portion 14 is expanded by the pre-curved portion 6 during insertion of the guide sheath 4, the groove portion 14 can be gradually expanded by the inclined surface 15 and consequently the insertion operation can be facilitated.

Figure 13:
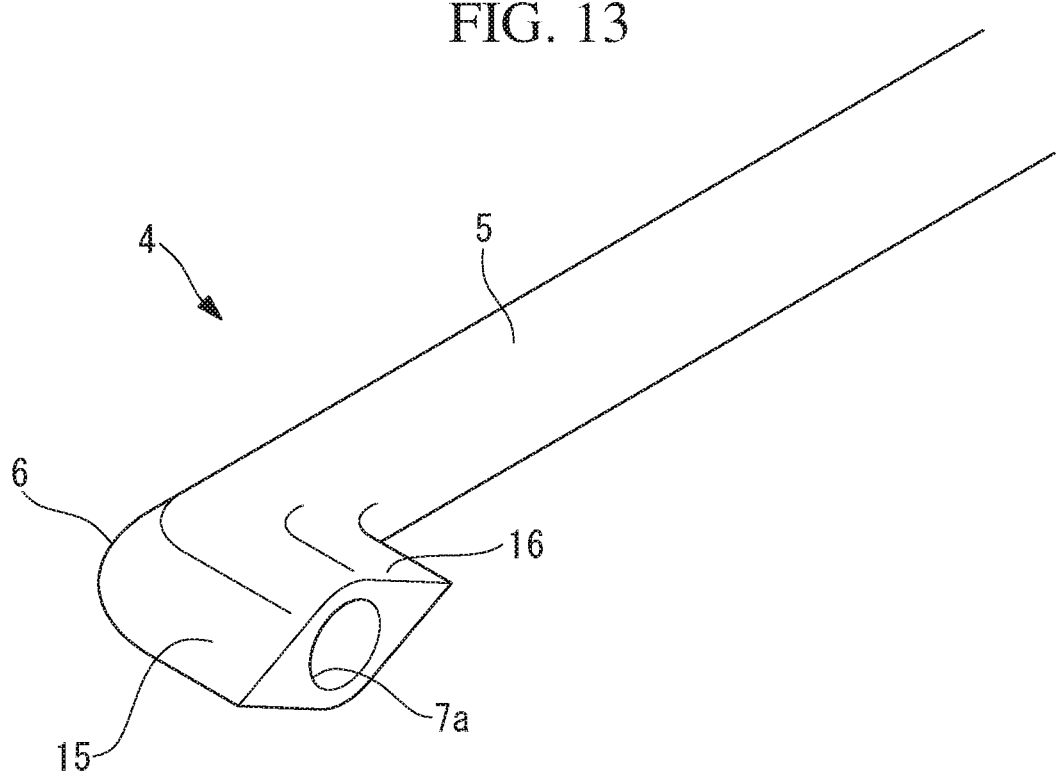
FIG. 13 is a partial perspective view illustrating another modification of the guide sheath in FIG. 2.

Alternatively, as illustrated in FIG. 13, the pre-curved portion 6 may have a cross-sectional shape that also has an inclined surface 16 that tapers rearward in the longitudinal axis direction of the sheath body 5. As a result, when the guide sheath 4 is retracted, while the groove portion 14 is expanded by the pre-curved portion 6 during retraction of the guide sheath 4, the groove portion 14 can be gradually expanded by the inclined surface 16, and consequently the pulling operation can be facilitated.

Figure 14:
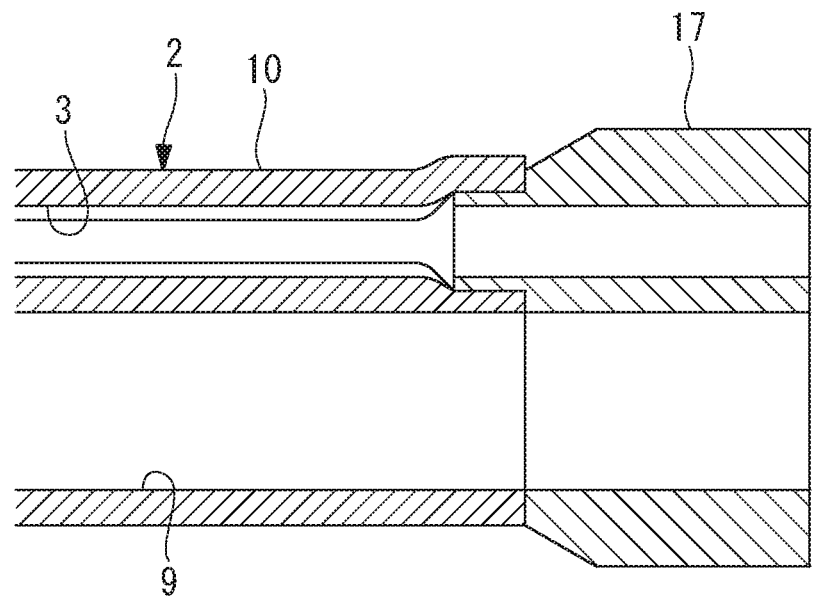
FIG. 14 is a partial vertical cross-sectional view illustrating a modification of the treatment system in FIG. 1, illustrating a state in which a base member is attached to a proximal end of the overtube.

As illustrated in FIG. 14, a base member 17 may be attached to the proximal end side of the overtube 2 so as to expand the groove width dimension of the groove portion 14 in a proximal-end-side opening of the first lumen 3 to be larger than an outer diameter dimension of the pre-curved portion 6. As a result, the guide sheath 4 can be inserted into the first lumen 3 expanded by the base member 17 without resistance, and the insertion operation can be facilitated.

Figure 15:
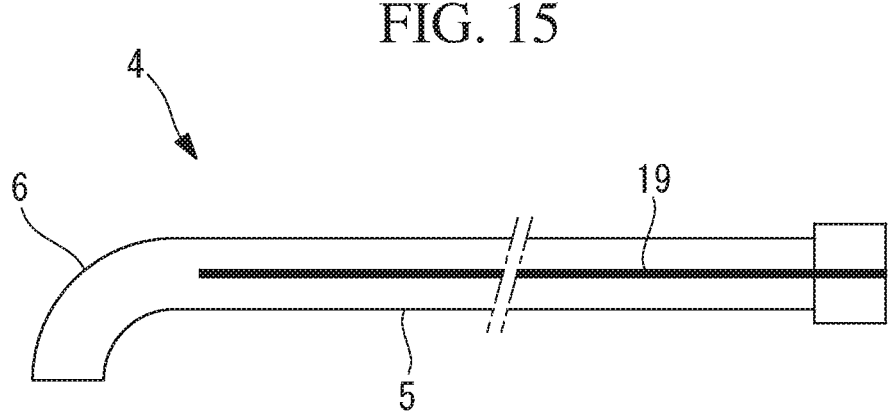
FIG. 15 is a side view illustrating a modification of the guide sheath in FIG. 2.
Figure 16:
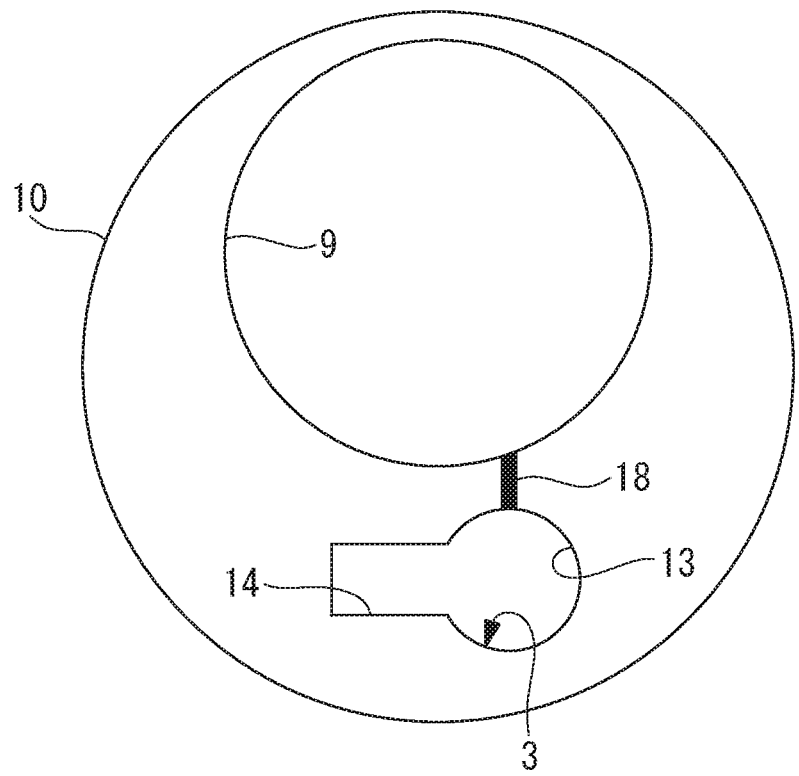
FIG. 16 is a view illustrating a proximal end surface of the overtube when the guide sheath in FIG. 15 is used.

As illustrated in FIGS. 15 and 16, marks 18 and 19 may be provided on the proximal end surface of the overtube 2 and the side surface of the guide sheath 4 so as to coincide with each other when the guide sheath 4 is advanced and retracted in the first lumen 3. Thereby, even after the pre-curved portion 6 is made to protrude forward from the distal end of the overtube 2, and the guide sheath 4 is rotated about the longitudinal axis, by aligning the mark 18 of the overtube 2 and the mark 19 of the guide sheath 4 on the proximal end side of the overtube 2 with each other, the guide sheath 4 can be easily disposed in a state in which it can be housed in the first lumen 3.

The shapes of the marks 18 and 19 may be arbitrary. As illustrated in FIG. 15, the mark 19 may be provided at one position in the circumferential direction of the sheath body 5 over substantially the entire length, or the mark 19 may be provided only over a predetermined length range on the proximal end side of the guide sheath 4.

Figure 17:
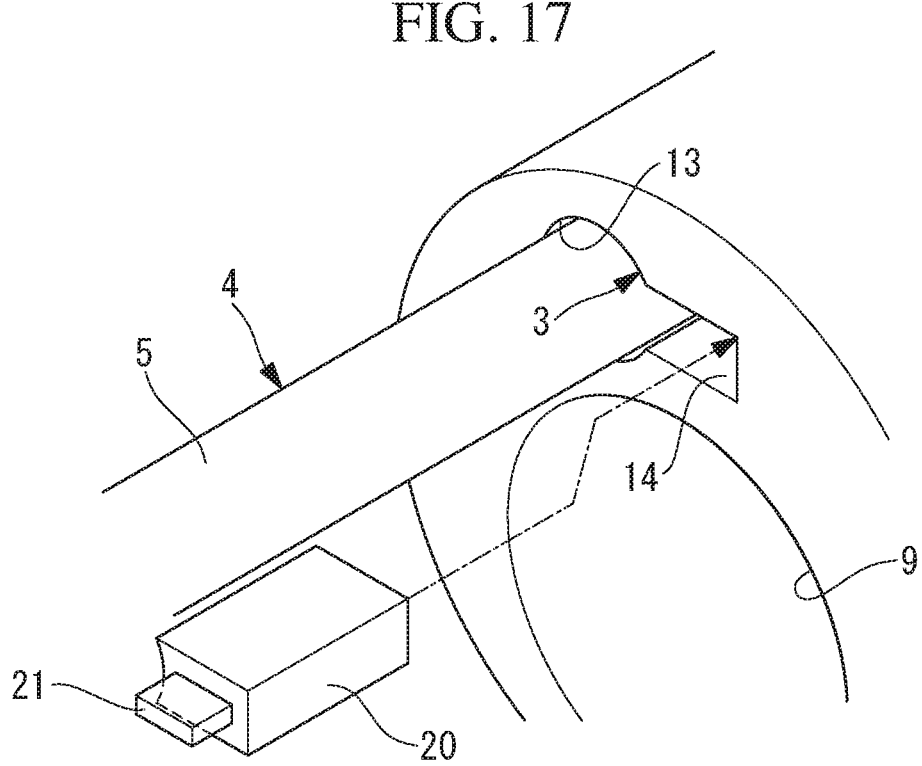
FIG. 17 is a partial perspective view of the proximal end of the overtube illustrating a modification of the treatment system in FIG. 1.

As illustrated in FIG. 17, in a state in which the guide sheath 4 has been inserted in the first lumen 3, a lid member (closing member) 20 that closes the groove portion 14 on the proximal end side of the overtube 2 may be provided. This can prevent gas or liquid from the body from leaking out of the body via the groove portion 14. In the figure, reference numeral 21 is a handle for handling the lid member 20.

Figure 18:
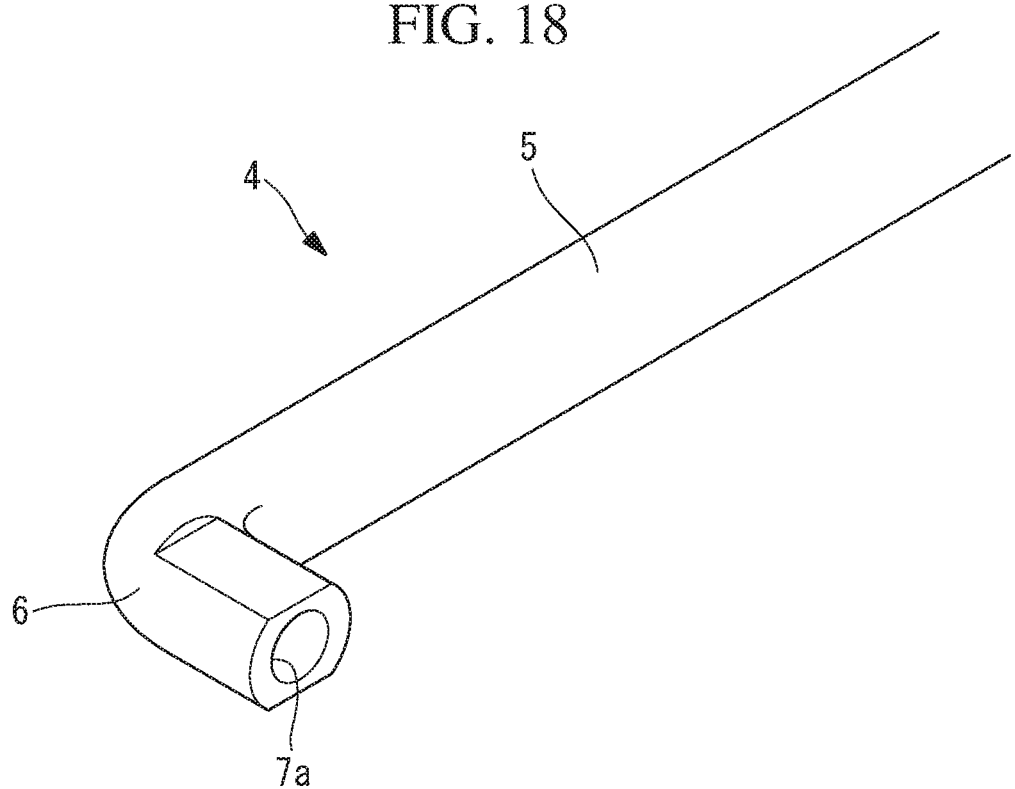
FIG. 18 is a partial perspective view illustrating a modification of the guide sheath in FIG. 2.

As illustrated in FIG. 18, the thickness dimension of the pre-curved portion 6 may be smaller than the groove width dimension of the groove portion 14. As a result, it is not necessary to perform insertion while expanding the groove portion 14 with the pre-curved portion 6, friction can be reduced, and insertion can be facilitated. In this case, only the thickness dimension of the pre-curved portion 6 may be reduced, or the outer diameter dimension of the pre-curved portion 6 may be reduced.

Figure 19:
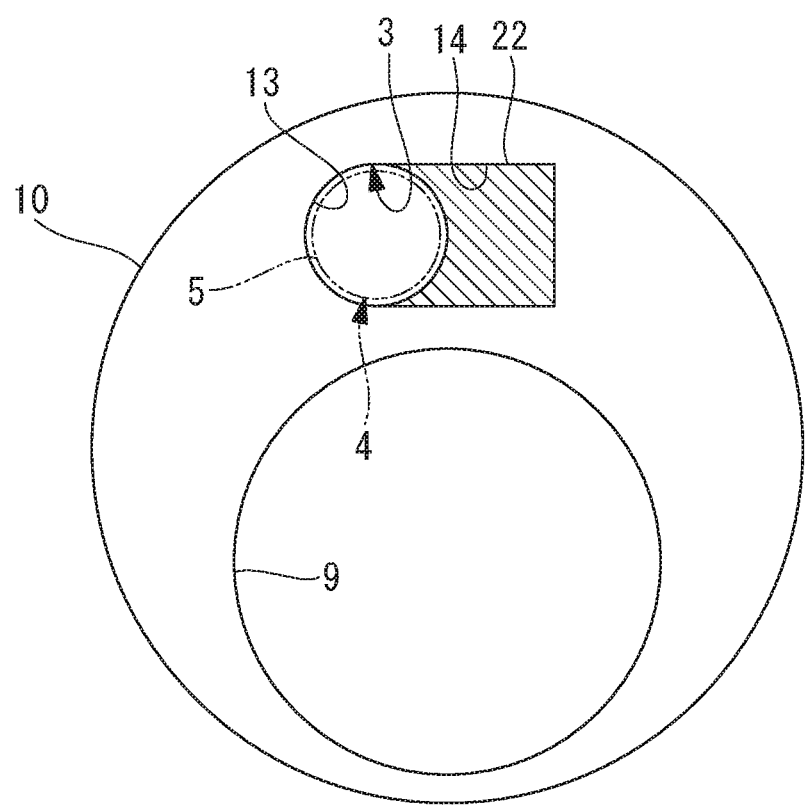
FIG. 19 is a front view of the proximal end surface of the overtube illustrating a modification of the treatment system in FIG. 1.
Figure 20:
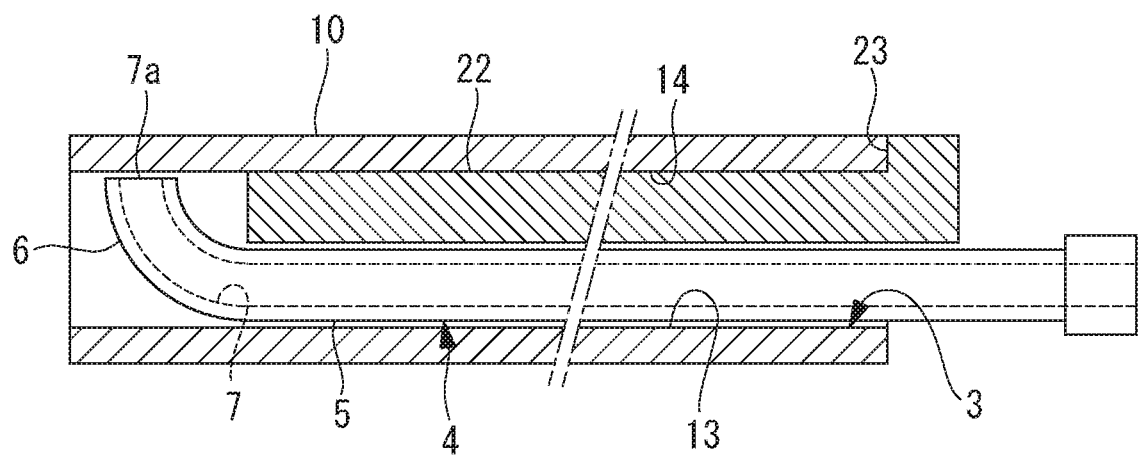
FIG. 20 is a vertical cross-sectional view illustrating the treatment system in FIG. 19.

As illustrated in FIGS. 19 and 20, in a state in which the groove width of the groove portion 14 of the first lumen 3 is set to be equal to or larger than the outer diameter dimension of the circular portion 13 and the guide sheath 4 has been inserted in the first lumen 3, a rod-shaped closing member 22 that is inserted into the first lumen 3 from the proximal end side and that has a cross-sectional shape that fills the groove portion 14 located on a proximal end side of the pre-curved portion 6 may be provided. Consequently, when the guide sheath 4 moves back and forth in the first lumen 3, the occurrence of friction can be reduced as much as possible, and the back and forth movement can be facilitated. In addition, after inserting the guide sheath 4 into the first lumen 3, the sheath body 5 can be held in a stable state within the circular portion 13 defined by the closing member 22, and it is possible to prevent the treatment tool 8 from moving in a direction not intended by the operator when a force is applied to a distal end of the treatment tool 8 during treatment. In FIG. 20, reference sign 23 denotes a stopper that fixes the closing member 22 at an appropriate insertion position.

Figure 21:
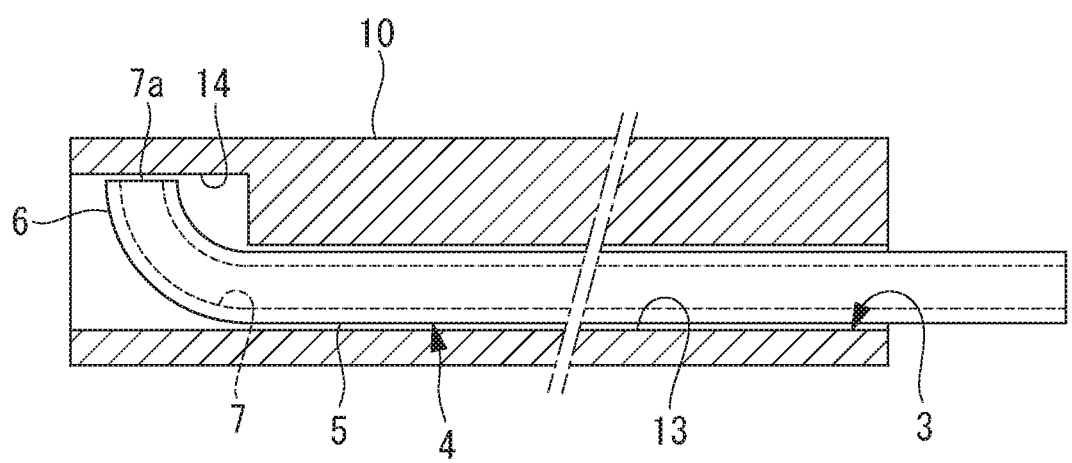
FIG. 21 is a vertical cross-sectional view illustrating a modification of the treatment system in FIG. 1.

As illustrated in FIG. 21, the first lumen 3 may include the circular portion 13 provided over the entire length of the overtube 2, and the groove portion 14 provided only over a predetermined length in the longitudinal axis direction from the distal end of the overtube 2 and recessed radially outward in at least a part of the circular portion 13 in the circumferential direction.

In this case, before inserting the overtube 2 into the body cavity Y, even though it is necessary to store the guide sheath 4 in the first lumen 3 from the distal end side of the overtube 2, the effect that the pre-curved portion 6 can be made to protrude from a distal end surface of the overtube 2 in a sufficiently curved state, and that the sheath body 5 can be firmly supported so as not to be displaced, is similar to that of the above-described embodiment.

In addition, because a step is formed on the proximal end side of the groove portion 14 by providing the groove portion 14 up to an intermediate position in the longitudinal axis direction, the pre-curved portion 6 can be reliably housed in the first lumen 3 by pulling the guide sheath 4 toward the proximal end side up to the position where it hits the step.

Figure 22:
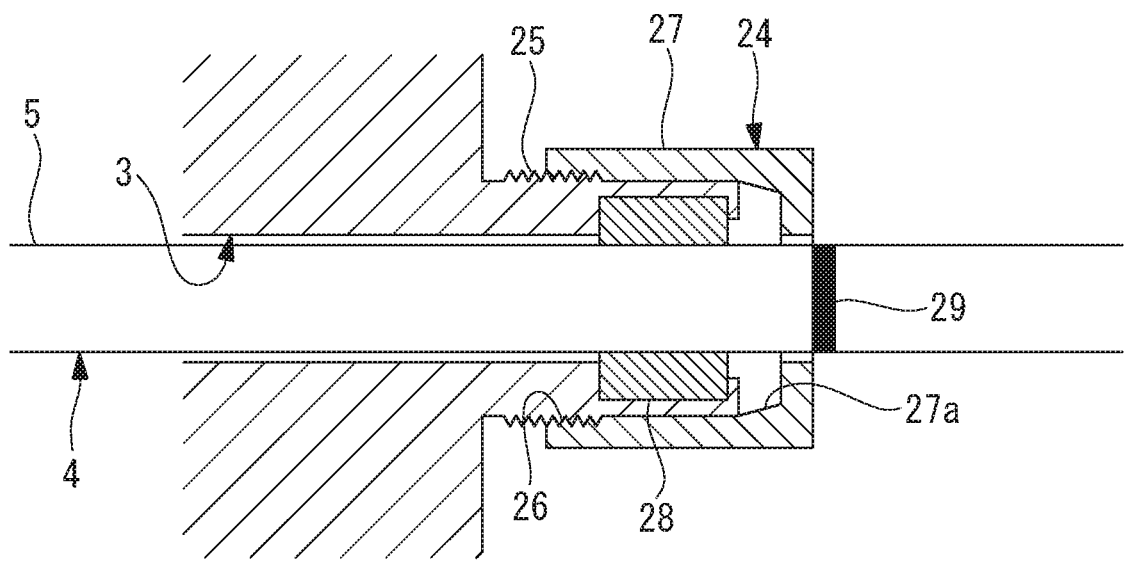
FIG. 22 is a partial longitudinal sectional view illustrating a lock mechanism in the treatment system in FIG. 21.

In addition, in the case of the treatment system 1 in which the guide sheath 4 is housed in the first lumen 3 in advance, as illustrated in FIG. 21, when inserting the overtube 2 into the body cavity Y, it is necessary to prevent the guide sheath 4 from unintentionally protruding from the distal end surface of the overtube 2. Therefore, for example, as illustrated in FIG. 22, a lock mechanism 24 for locking the guide sheath 4 may be provided at the opening position of the first lumen 3 disposed on the proximal end side of the overtube 2.

The lock mechanism 24 may be, for example, one including a male screw 25 fixed at an opening position of the first lumen 3, a female screw 26 formed in a cylindrical shape that penetrates the guide sheath 4 and that is fastened to the male screw 25, a cap 27 having a tapered inner surface 27*a*, and a cylindrical elastic member arranged between the cap 27 and the guide sheath 4. By fastening the female screw 26 of the cap 27 to the male screw 25, an elastic member 28 is contracted radially inward by the tapered inner surface 27*a* provided on the inner peripheral surface of the cap 27, and the elastic member 28 is brought into close contact with the outer peripheral surface of the guide sheath 4. Thereby, the guide sheath 4 can be fixed to the overtube 2. In the figures, reference sign 29 is a mark provided on the outer peripheral surface of the guide sheath 4 and indicates that the guide sheath 4 is housed in the first lumen 3.

Figure 23:
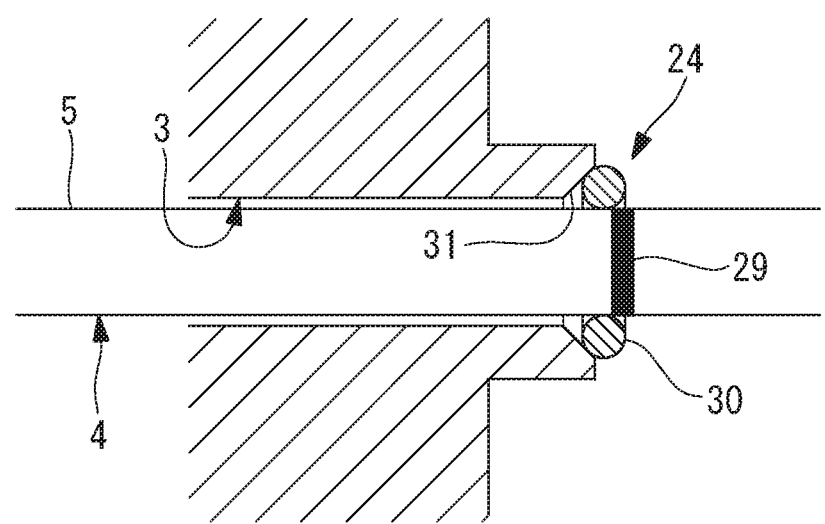
FIG. 23 is a partial vertical cross-sectional view illustrating another example of the lock mechanism in FIG. 22.

As illustrated in FIG. 23, a lock mechanism having an O-ring 30 attached to the outer peripheral surface of the guide sheath 4 and a tapered inner surface 31 provided at the opening position of the first lumen 3 may be adopted as the lock mechanism 24.

The above-described embodiment also leads to the following aspects.

According to an aspect of the present invention, a treatment system includes a guide sheath having a pre-curved portion that has been preliminarily curved in a direction intersecting a longitudinal axis at a distal end of a tubular sheath body having the longitudinal axis; and an overtube having a first lumen through which the guide sheath is passed and a second lumen through which an endoscope is passed, wherein an inner peripheral surface defining the first lumen has a cross-sectional shape capable of housing the guide sheath in a state where the pre-curved portion remains curved.

According to this aspect, the endoscope that has been passed through the second lumen, and the pre-curved portion at the distal end of the guide sheath that has been passed through the first lumen are exposed from the distal end of the overtube positioned in a body cavity, and while observing the inside of the body cavity using the endoscope, tissue inside the body cavity can be treated using a treatment tool that has been passed through the inside of the guide sheath. Since the treatment tool that is passed through the tubular guide sheath becomes curved in accordance with the curved shape of the pre-curved portion and protrudes in an opening direction from a distal end of the pre-curved portion without having its own curving mechanism, it is possible to easily treat the tissue inside the body cavity, which is located forward in the opening direction.

In this case, since the cross-sectional shape of the inner peripheral surface that defines the first lumen is formed into a shape that is capable of housing the guide sheath in a state where the pre-curved portion remains curved, even when the guide sheath is housed in the first lumen, it is not necessary to apply an external force to the pre-curved portion in order to straighten the curve. This improves the insertability of the guide sheath through the first lumen of the overtube, and it is possible to achieve a desired curved shape of the pre-curved portion at the position where the pre-curved portion has been made to protrude from the distal end of the overtube.

In the above aspect, the outer peripheral surface of the overtube, the inner peripheral surface defining the first lumen, and an inner peripheral surface defining the second lumen may be integrally formed in the overtube.

In addition, in the above aspect, the inner peripheral surface defining the first lumen may have a constant cross-sectional shape in a direction orthogonal to the longitudinal axis over an entire length of the overtube, and the cross-sectional shape may include a circular portion having an inner diameter dimension larger than an outer diameter dimension of the sheath body, and a groove portion that is recessed radially outward in at least a part of the circular portion in a circumferential direction.

With this configuration, from a proximal end side of the overtube that has been positioned inside the body cavity, it is possible to dispose the sheath body in the circular portion of the first lumen, dispose the pre-curved portion in the groove portion of the first lumen, insert the guide sheath into the first lumen, and make the pre-curved portion protrude from the distal end of the overtube.

In addition, in the above aspect, the cross-sectional shape of the first lumen may have a first dimension along a first direction, which is an arrangement direction of the first lumen and the second lumen, and a second dimension, which is larger than the first dimension and which extends along a second direction intersecting the first direction, and the groove portion may be recessed in the second direction.

In addition, in the above aspect, the groove portion may be recessed more than a length by which the pre-curved portion protrudes from the sheath body in a radial direction.

With this configuration, since the groove portion is recessed radially outward from an inner peripheral surface of the circular portion by a length greater than the length by which the pre-curved portion protrudes from the sheath body in the radial direction, the pre-curved portion can be housed in the groove portion without having to straighten the curve.

In addition, in the above aspect, the groove portion may have a groove width dimension smaller than the outer diameter dimension of the sheath body.

With this configuration, when the guide sheath is inserted forward from the proximal end side of the overtube in the first lumen, the rotation of the pre-curved portion about the longitudinal axis is maintained in a restricted state. In addition, even after the pre-curved portion is made to protrude from the distal end of the overtube, the sheath body of the guide sheath can be supported in a stable state without slipping from the circular portion to the groove portion side.

In addition, in the above aspect, the overtube may be formed of an elastic material having a hardness lower than that of the guide sheath, and the groove portion may have a groove width dimension smaller than an outer diameter dimension of the pre-curved portion.

With this configuration, when the pre-curved portion is inserted into the groove portion, the pre-curved portion is inserted while elastically deforming and expanding the groove portion. Thereby, the guide sheath is stably supported in the first lumen.

In addition, in the above aspect, the overtube may be formed of an elastic material having a Shore hardness of 35A or more and 45A or less, and the guide sheath may be formed of a material having a Shore hardness of 65D or more and 75D or less.

In addition, in the above aspect, the groove width dimension of the groove portion may be 40% or more and 60% or less of a diameter dimension of the sheath body.

In addition, in the above aspect, the treatment system may further include a base member that is attached to the proximal end side of the overtube and that expands the groove width dimension of the groove portion in an opening on a proximal end side of the first lumen so as to be larger than the outer diameter dimension of the pre-curved portion.

With this configuration, when inserting the pre-curved portion into the groove portion having a groove width dimension smaller than the outer diameter dimension of the pre-curved portion, the base member expands the opening on the proximal end side of the first lumen, thereby improving ease of insertion.

In addition, in the above aspect, the pre-curved portion may have an inclined surface that forms a cross-sectional shape of the pre-curved portion so as to taper in a direction along the longitudinal axis of the guide sheath.

With this configuration, when inserting the pre-curved portion into the groove portion, it is possible to insert the pre-curved portion while gradually widening the groove portion by the inclined surface, and it is possible to improve the ease of insertion.

In addition, in the above aspect, a cross-sectional shape of the inner peripheral surface defining the first lumen in a direction orthogonal to the longitudinal axis may include a circular portion having an inner diameter dimension larger than an outer diameter dimension of the sheath body, and a groove portion that is recessed radially outward in at least a part of the circular portion in a circumferential direction, the groove portion may have a groove width dimension larger than an outer diameter dimension of the pre-curved portion, and in a state where the guide sheath has been inserted in the first lumen, a closing member may be inserted into the first lumen from a proximal end side and may have a cross-sectional shape that fills the groove portion disposed on a proximal end side of the pre-curved portion.

With this configuration, when inserting the guide sheath into the first lumen, it is easy to insert the guide sheath through the groove portion having a groove width dimension larger than an outer diameter dimension of the pre-curved portion with the closing member removed from the first lumen. Then, after the guide sheath has been inserted into the first lumen, it is possible to insert the closing member into the groove portion from the proximal end side of the first lumen and fill the groove portion disposed on a proximal end side of the pre-curved portion with the closing member.

Accordingly, even after the pre-curved portion has been made to protrude from the distal end of the overtube, the sheath body of the guide sheath can be supported in a stable state without slipping from the circular portion to the groove portion side.

In addition, in the above aspect, the inner peripheral surface defining the first lumen may include a circular portion provided over an entire length of the overtube and having a circular cross-sectional shape with an inner diameter dimension larger than an outer diameter dimension of the sheath body, and a groove portion that is provided only over a predetermined length in a direction of the longitudinal axis from the distal end to a proximal end of the overtube and that is recessed radially outward from the inner peripheral surface in at least a part of the circular portion in a circumferential direction, the recessed portion being larger than a length by which the pre-curved portion protrudes from the sheath body in a radial direction.

With this configuration, before inserting the overtube into the body cavity, when the sheath body of the guide sheath is inserted into the circular portion of the first lumen from the distal end side of the overtube, the pre-curved portion that curves from the sheath body is housed in the first lumen in a state of being inserted into the groove portion. Consequently, by inserting the guide sheath from the distal end side of the overtube, the pre-curved portion can be housed in the first lumen while being curved, and, at the time of treatment, a desired curved shape of the pre-curved portion can be achieved at the position where the pre-curved portion has been made to protrude from the distal end of the overtube.

REFERENCE SIGNS LIST 1 treatment system
2 overtube
3 lumen (first lumen)
4 guide sheath
5 sheath body 6 pre-curved portion
9 lumen (second lumen)
10 multi-lumen tube
12 endoscope
13 circular portion
14 groove portion
15 inclined surface
17 base member
20 lid member (closing member)
22 closing member

The invention claimed is:

1. A treatment system comprising:
a guide sheath comprising:
a main body extending along a longitudinal axis;
an offset portion disposed on a distal end of the main body and offset in a direction intersecting the longitudinal axis; and
an overtube comprising:
a first lumen through which the guide sheath is passed; and
a second lumen configured to accommodate an endoscope therein, the second lumen being separately formed and radially offset from the first lumen;
wherein the first lumen has a cross-sectional shape configured to house the guide sheath in a state where the offset portion remains offset.

2. The treatment system according to claim 1, wherein the first lumen and the second lumen are integrally formed in the overtube.

3. The treatment system according to claim 2, wherein the overtube is formed of an elastic material having a Shore hardness of 35A or more and 45A or less, and
the guide sheath is formed of a material having a Shore hardness of 65D or more and 75D or less.

4. The treatment system according to claim 2, wherein the first lumen has a cross-sectional shape in a direction orthogonal to the longitudinal axis over an entire length of the overtube, and
the cross-sectional shape includes a circular portion having an inner diameter larger than an outer diameter of the sheath body, and a groove portion in communication with the circular portion, the groove portion extending outward from a central axis of the circular portion.

5. The treatment system according to claim 4, wherein the circular portion has a first dimension and is radially offset from the second lumen in both a first direction and a second direction intersecting the first direction, and
the groove portion extends from the circular portion in the second direction for a second dimension.

6. The treatment system according to claim 5, wherein the second dimension is longer more than a length by which the offset portion protrudes from the sheath body in a radial direction.

7. The treatment system according to claim 5, wherein a width dimension of the groove portion along the first direction is smaller than the outer diameter of the sheath body.

8. The treatment system according to claim 7, wherein the overtube is formed of an elastic material having a hardness lower than that of the guide sheath.

9. The treatment system according to claim 8, wherein the offset portion has an inclined surface that forms a cross-sectional shape of the offset portion so as to taper in a direction along the longitudinal axis of the guide sheath.

10. The treatment system according to claim 7, wherein the width dimension of the groove portion along the first direction is 40% or more and 60% or less of the outer diameter of the sheath body.

11. The treatment system according to claim 10, further comprising a base member that is attached to a proximal end side of the overtube and that expands the second dimension in an opening on a proximal end side of the first lumen so as to be larger than the outer diameter of the sheath body.

12. The treatment system according to claim 5, further comprising a closing member,
wherein in a state where the guide sheath is inserted in the first lumen, the closing member is inserted into the first lumen from a proximal end side, and the closing member is configured to fill at least part of the groove portion disposed proximally relative to the offset portion.

13. The treatment system according to claim 1, wherein an inner peripheral surface of the first lumen includes:
a circular portion provided over an entire length of the overtube and having a circular cross-sectional shape with an inner diameter larger than an outer diameter of the sheath body, and
a groove portion extending distally from a distal end face of the overtube, and the groove portion extending outward from at least a part of the inner peripheral surface of the circular portion, the groove portion extending in a radial direction for a length larger than a length by which the offset portion protrudes from the sheath body.

14. The treatment system according to claim 1, wherein the guide sheath further comprising a lumen formed to extend through both the main body and the offset portion, the lumen being configured to guide a treatment tool distally of a distal end of the overtube.

15. An overtube comprising:
an elongated tube body extending along a longitudinal axis, the tube body having a first lumen and a second lumen extending in a longitudinal axis direction,
wherein the first lumen has a cross-sectional shape in a direction orthogonal to the longitudinal axis over a longitudinal length of the tube body,
the cross-sectional shape includes a circular portion and a groove portion extending outward from at least a part of an inner peripheral surface of the circular portion; and
a proximal end extension attached to a proximal end of the elongated tube body, the proximal end extension having a third lumen in communication with the second lumen and a fourth lumen in communication with the first lumen, the fourth lumen having a cross-sectional shape larger than the cross sectional shape of the first lumen.

16. The overtube according to claim 15, wherein the circular portion has a first dimension and is offset radially from the second lumen in both a first direction and a second direction intersecting the first direction, and
the groove portion extends from the circular portion in the second direction for a second dimension.

17. The overtube according to claim 16, wherein the second dimension is longer more than a length by which the offset portion protrudes from the sheath body in a radial direction.

18. The overtube according to claim 15, wherein a width dimension of the groove portion along the first direction is smaller than the outer diameter of the sheath body.

19. The overtube according to claim 15, wherein the circular portion has an inner diameter larger than an outer diameter of the second lumen.

* * * * *